US010932751B2

(12) United States Patent
Boctor et al.

(10) Patent No.: US 10,932,751 B2
(45) Date of Patent: Mar. 2, 2021

(54) CATHETER ULTRASOUND TRANSMISSION ELEMENT (CUTE) CATHETER

(71) Applicant: THE JOHNS HOPKINS UNIVERSITY, Baltimore, MD (US)

(72) Inventors: Emad Boctor, Baltimore, MD (US); Ralph Etienne-Cummings, Washington, DC (US); Jairo Garcia, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 419 days.

(21) Appl. No.: 15/722,109

(22) Filed: Oct. 2, 2017

(65) Prior Publication Data

US 2018/0116629 A1 May 3, 2018

Related U.S. Application Data

(60) Provisional application No. 62/402,307, filed on Sep. 30, 2016.

(51) Int. Cl.
*A61B 8/12* (2006.01)
*A61B 8/08* (2006.01)
(Continued)

(52) U.S. Cl.
CPC .............. *A61B 8/12* (2013.01); *A61B 5/0095* (2013.01); *A61B 5/4325* (2013.01);
(Continued)

(58) Field of Classification Search
CPC ....... A61B 8/12; A61B 8/4416; A61B 8/0841; A61B 8/445; A61B 34/20; A61B 5/4325;
(Continued)

(56) References Cited

U.S. PATENT DOCUMENTS

| 7,575,550 B1 * | 8/2009 | Govari ..................... A61B 5/06 600/424 |
| 2001/0031919 A1 * | 10/2001 | Strommer .............. A61B 34/20 600/424 |

(Continued)

*Primary Examiner* — Bo Joseph Peng
(74) *Attorney, Agent, or Firm* — Harrity & Harrity, LLP

(57) ABSTRACT

An embodiment in accordance with the present invention provides a precise catheter tracking system, Active Ultrasound Pattern Injection System (AUSPIS). AUSPIS establishes ultrasonic communication between any ultrasound external probe and internal catheter (CUTE catheter). The system receives image beacon pulses, analyzes the acquired signal, and fires one or a series of active echo pulses from the same active echo element with a proper timing, frequency, duration and amplitude. Thus it enables injection of any "virtual" pattern into the B-mode image. The pattern injected to the B-mode image is from actively encoded ultrasound field in the tissue. The encoding is based on B-mode ultrasound image formation technique, so it doesn't require hardware or software modification to the US machine. It continuously measures the local acoustic signal amplitude, by which sub-millimeter elevation localization accuracy can be achieved. The technique can be used for tracking, tool guidance, and annotation with configured tracking formations.

6 Claims, 7 Drawing Sheets

(51) Int. Cl.
*A61B 34/20* (2016.01)
*A61B 5/00* (2006.01)
*A61B 8/00* (2006.01)
*A61B 90/00* (2016.01)

(52) U.S. Cl.
CPC .......... *A61B 5/6852* (2013.01); *A61B 8/0841* (2013.01); *A61B 34/20* (2016.02); *A61B 8/445* (2013.01); *A61B 8/4416* (2013.01); *A61B 2034/2063* (2016.02); *A61B 2034/2065* (2016.02); *A61B 2090/378* (2016.02); *A61B 2090/3929* (2016.02)

(58) Field of Classification Search
CPC ................ A61B 5/0095; A61B 5/6852; A61B 2090/378; A61B 2090/3929; A61B 2034/2063; A61B 2034/2065
See application file for complete search history.

(56) References Cited

U.S. PATENT DOCUMENTS

| | | | |
|---|---|---|---|
| 2002/0173720 A1* | 11/2002 | Seo | A61B 8/483 600/437 |
| 2003/0100938 A1* | 5/2003 | Rubenchik | A61B 5/02007 623/1.1 |
| 2009/0266957 A1* | 10/2009 | Cermak | A61B 8/4281 248/225.11 |
| 2011/0265570 A1* | 11/2011 | Kumazawa | A61B 8/58 73/627 |
| 2013/0041252 A1* | 2/2013 | Vignon | A61B 8/0841 600/424 |
| 2015/0031990 A1* | 1/2015 | Boctor | A61B 8/483 600/424 |
| 2015/0150464 A1* | 6/2015 | Boctor | A61B 5/0095 600/424 |
| 2016/0228090 A1* | 8/2016 | Boctor | A61B 8/4416 |

* cited by examiner

CATHETER ULTRASOUND TRANSMISSION ELEMENT (CUTE) CATHETER

CROSS REFERENCE TO RELATED APPLICATIONS

This application claims the benefit of U.S. Provisional Patent Application No. 62/402,307, filed on Sep. 30, 2016, which is incorporated by reference herein, in its entirety.

FIELD OF THE INVENTION

The present invention relates generally to medical devices. More particularly, the present invention relates to a catheter ultrasound transmission element (CUTE) catheter.

BACKGROUND OF THE INVENTION

According to the World Health Organization, infertility is "a disease of the reproductive system defined by the failure to achieve a clinical pregnancy after 12 months or more of regular unprotected sexual intercourse." Approximately 48.5 million couples are infertile worldwide. And about 15% of couples in the United States are involuntarily infertile. In the US, more than one million couples seek infertility treatment each year, and spend more than $3 billion in pursuit of babies.

The cause of infertility and the subsequent suggested treatment's pathway is determined by the evaluation of both the man and woman. Approximately 40% of infertility cases is related to the woman, 40% is related to the male-factor, and about 20% is attributed to both. Professional intervention can help about 40% of these couples achieve a pregnant state. This clinical service and professional intervention is provided through fertility clinics. In 1985, there were 30 fertility clinics in the U.S. A decade later, there were more than 300, and in 2013, there were 481.

Depending on the cause of infertility, treatment can have various forms and options from consultation, medication, to artificial insemination, or at the end relying on assistive reproductive techniques. A typical treatment protocol can start with Intrauterine Insemination (IUI) where the semen is placed through the cervix into the uterine cavity by means of a sterile transcervical catheter as shown in FIG. 1. FIG. 1 illustrates a partially sectional view of intrauterine insemination. This artificial insemination approach has several advantages including: a) relatively inexpensive procedure (~$2000 per cycle); b) insurance coverage is widely available; c) minimal hormonal excitation; and d) quick outpatient operation. Unfortunately, however, this treatment has a low success rate. It is known to have 4% success rate per cycle without hormonal excitation; 10% success rate per cycle with hormonal intake; and with hyper stimulation, it can reach 15% success rate with the risk of administrating high-dosage of hormones and multiple pregnancy. This treatment protocol can be repeated for 4-8 cycles.

When the IUI approach doesn't lead to a pregnant state or is not recommended due to a low sperm count, an assistive reproductive technique (ART) is usually suggested for the infertile couple to pursue. In Vitro Fertilization (IVF) approach is the most common ART techniques, where the ovaries are hyperstimulated with agents to induce follicle formation, follicle development is monitored daily, the ovum is removed from the ovary just prior to ovulation, it is fertilized in vitro and then it is placed into the uterine cavity for implantation. The embryo is transferred by a catheter very similar to the one shown in FIG. 1. IVF has a substantially higher success rate compared to IUI, reaching as high as 32.75% per cycle. Several serious disadvantages limit this approach including: a) high-cost—around $18000; b) limited insurance and only available in 26 States; c) high-dose of hormone; d) some religious barriers; and e) available only in centers with sophisticated labs carrying and processing embryos.

Gamete Intrafallopian Transfer (GIFT) is an alternative to IVF. In GIFT, fertilization by the sperm does not take place in vitro in the laboratory. Instead, the mixture of sperm and the oocytes are loaded into a catheter and, through laparoscopy as shown in FIG. 2, two oocytes and about 100,000 motile sperm are introduced for a short distance into the fimbriated end of each uterine tube. It has a similar success rate to IVF and it doesn't require sophisticated lab leading to potential lower-cost and hormonal intake. FIG. 2 illustrates a partially sectional view of GIFT. This approach is also tolerated by many religions. The main disadvantage is the invasiveness of this laparascopic surgical procedure. In most hospitals, it is hard to schedule a surgery room within few hours, adding a serious logistic challenge for GIFT procedures that require fast response time.

There is a clear clinical need to increase fertilization success rate in a non-surgical and easy-to-perform approach, while decreasing the number of cycles/trials and hence reducing both cost and hormone intake. Fertilization success rate varies from 22% per cycle for normal population, i.e. fertile couple, to 10% per IUI cycle with hormone, and to 35% per IVF cycle. The best fertilization rate of 75%, however, happens in in vitro assay by accumulating 10000 sperms with an egg in a 50 µL volume; and with a male-factor, the protocol suggests adding 50000 sperms with an egg in the same 50 µL volume. Clearly and logically, this high success rate is attributed to both the high sperm count density (sperms per unit volume) and the targeting and delivery very close to the egg.

Therefore, it would be advantageous to provide a catheter with an ultrasound transmission element (CUTE).

SUMMARY OF THE INVENTION

The foregoing needs are met, to a great extent, by the present invention, wherein in one aspect a system includes a catheter having an active ultrasound element. The system also includes a catheter tracker. The catheter tracker establishes an ultrasonic communication between an external ultrasound probe and the catheter having the active ultrasound element. The catheter tracker receives image beacon pulses and analyzes the acquired signal. The catheter tracker also fires a series of active echo pulses from the active ultrasound element.

In accordance with an aspect of the present invention, the series of active echo pulses has a predetermined timing, frequency, duration, and amplitude. A virtual pattern is injected into a B-mode image. The virtual pattern is generated from an actively encoded ultrasound field in tissue. Encoding is based on B-mode ultrasound imaging technique.

In accordance with another aspect of the present invention, the system includes a pair of receiving elements. The system includes an ultrasound probe. The system can include a bracket coupled to the ultrasound probe configured to triangulate a position of the ultrasound probe. The system can include executing 3D beamforming to identify an ultrasound spot (from a catheter or PA activity) and accurately triangulate with respect to the US image frame. The system can also include executing a tracking algorithm to identify an ultrasound spot (from a catheter or PA activity) and accurately triangulate with respect to the US image frame. The system can include modulating a point signal source with a pre-determined frequency, such that a produced ultrasound wave will also be a pulse sequence with exactly the same modulation frequency. The system includes a pulse laser diode (PLD) and PLD driver. The system can include the PLD driver implementing a burst signal sequence. A non-transitory computer readable medium is configured for implementing the system. The catheter is configured for use in the uterus. A photoacoustic element is included and retained as a source of transmitting Omni directional ultrasound signal. The system is configured for in-plane and limited out-of-plane navigation accuracy of 1-2 mm with a frame rate higher than 10 Hz. The system is configured for extended tracking navigation accuracy of 2-4 mm with 10 Hz update and +/−50 mm out-of-plane tracking range. The system further includes the PLD being coupled to a small optical fiber (diameter 100-200 μm), where an end of the PLD is coated with a photoacoustic sensitive material. The photoacoustic sensitive material is chosen from a group of India-ink, PDMS with carbon black, or even a dichroic filter that completely absorbs 532 nm wavelength and it is transparent to NIR range, allowing PA and optical biopsy usage in the future.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
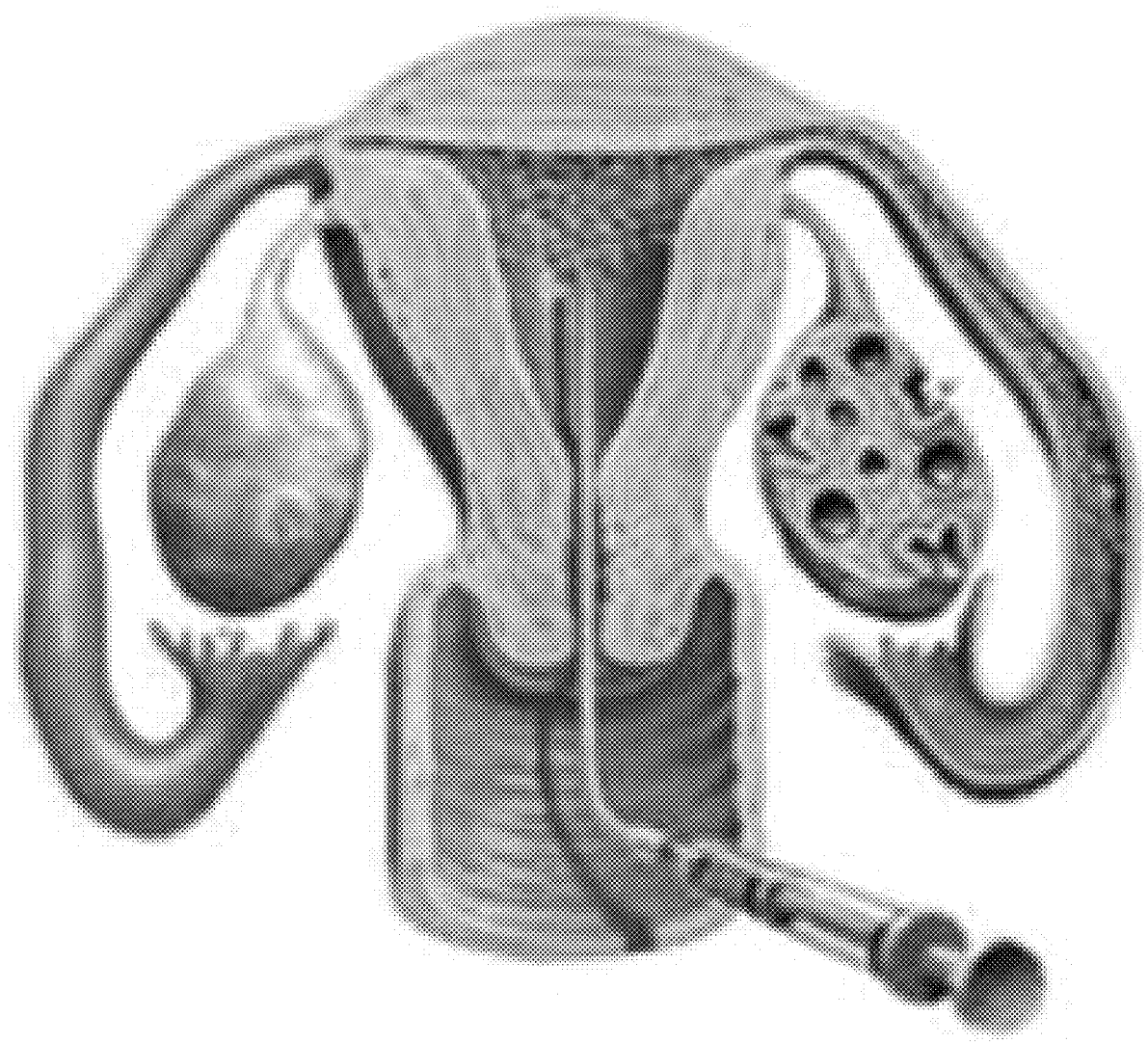
FIG. 1 illustrates a partially sectional view of intrauterine insemination.
Figure 2:
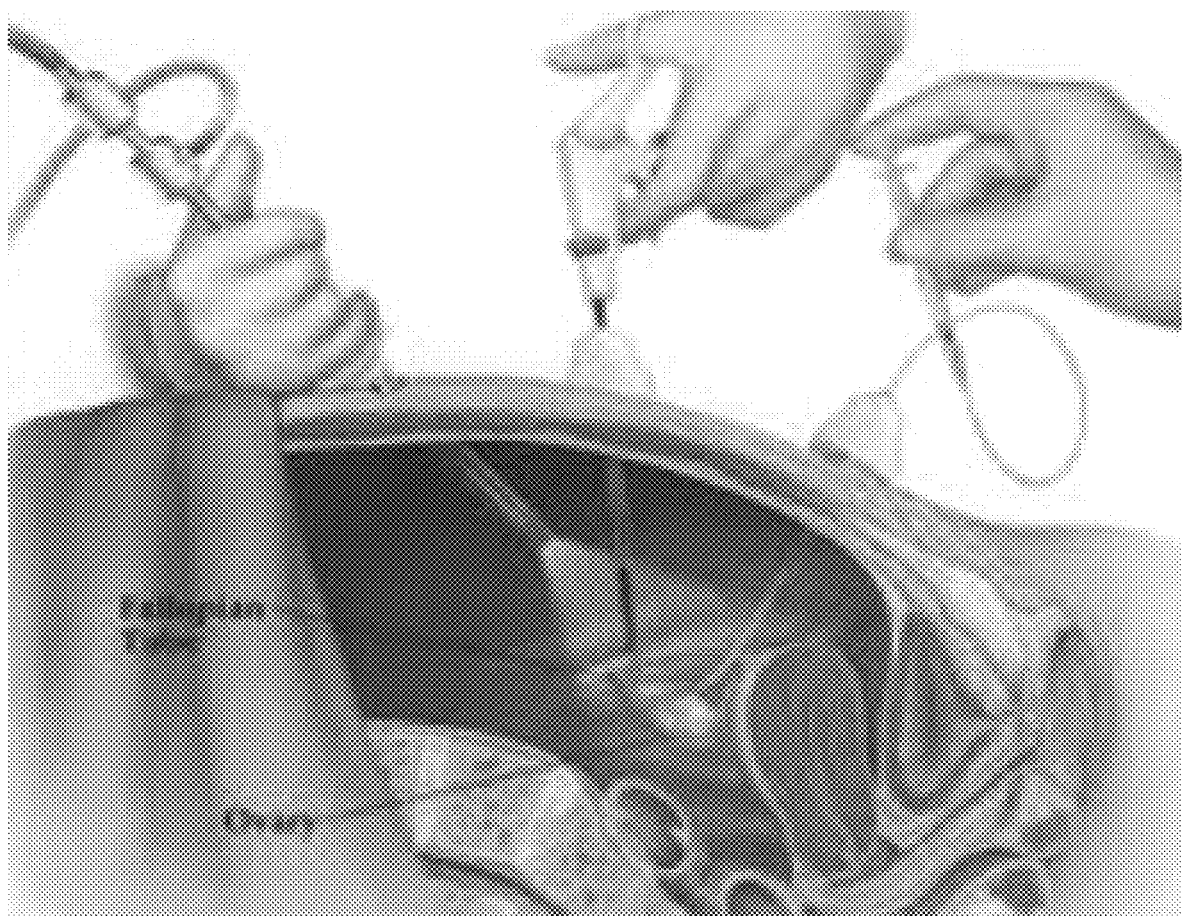
FIG. 2 illustrates a partially sectional view of GIFT.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a precise catheter tracking system, called Active Ultrasound Pattern Injection System (AUSPIS), by establishing an ultrasonic communication between any ultrasound external probe and internal catheter (CUTE catheter). The system receives the image beacon pulses, analyzes the acquired signal, and fires one or a series of active echo pulses from the same active echo element with a proper timing, frequency, duration and amplitude. Thus it enables us to inject any "virtual" pattern into the B-mode image. The pattern injected to the B-mode image is from the actively encoded ultrasound field in the tissue. The encoding is based on the B-mode ultrasound image formation technique, so it doesn't require any hardware or software modification to the US machine. It continuously measures the local acoustic signal amplitude, by which sub-millimeter elevation localization accuracy can be achieved. By configuring the pattern formations, the technique can be used for tracking, tool guidance, and annotation. Additionally, the 3D tracking methods of the present invention are US vendor independent, providing accurate 3D localization in- and out-of-plane. Most importantly, both H/W and S/W have been developed to allow innovation in execution without interrupting the current infertility clinical protocols.

Moving from in vitro assay to clinical studies, literature supports and confirms that delivering high-sperm count close to the egg always lead to higher success rate. There are large numbers of studies and papers investigate the effect of sperm count on IUI success. A recent study, reports that the cumulative pregnancy rate after four cycles of IUI was 17.3% in couple with at least one total motile count <1 million and 25.5% in couples with a total motile count consistently >1 million. This study and others are in-line with the logical intuition that high sperm count should increase the probability of sperms travelling up to the Fallopian tubes where the eggs can be fertilized. Unsurprisingly, the IUI limited pregnancy rates are attributed to the suboptimal sperm count at the site of fertilization. An alternative procedure termed Fallopian tube Sperm Perfusion (FSP), has been reported with improved pregnancy rates in comparison with IUI. In FSP sperm preparation is identical to the used with IUI, but the sperms are diluted in a larger volume of medium up to 4 ml. This volume has been considered sufficient for bilateral passage of the sperms through the Fallopian tubes. Theoretically this would increase the presence of sperms near the oocytes and results in the higher pregnancy rates. FSP clearly has an advantage in delivering sperms to the Fallopian, but the density and the count of sperms are not maintained within the appropriate tube. The execution of the FSP protocol is very difficult and the results are not consistently the same due to several factors including sperm leakage from the cervix and Fallopian tubes, the egg can move due to fluid pressure, and sperm/volume ratio at the egg site is considered small.

Building on the two aforementioned studies (sperm-count effect and the FSP approach), an artificial insemination approach is needed where a catheter is guided under external ultrasound imaging to deliver a concentrated sperm count at the entrance of the appropriate Fallopian tube. Ultrasound is the standard imaging modality in infertility treatment centers. There is a large volume of literature that have studied the effect and influence of US-guided artificial insemination on pregnancy rates. One recent study reports that ultrasound guidance improves pregnancy rates only when a senior provider performs the IUI procedure, implying that experience of the provider physician is a key factor to the IUI's success. This is logical as it is hard for junior provider to interpret US images correctly. Additionally, these catheters are very small and hard to visualize under ultrasound given an US beam thickness and limited lateral resolution. Experienced users often rely on indirect effects to better visualize the catheter tip—for example trying to monitor fluid motion during sperm injection. Similarly, the impact of the physician performing embryo transfer on pregnancy rates has been studied in ART. It was shown that outcomes of IVF vary depending on the provider physician. For every additional millimeter embryos are deposited away from the fundus—to reduce contraction—the odds of clinical pregnancy increased by 11%. Such a study is highlighting the importance of precise targeting and localization for both artificial insemination catheters carrying sperms and ART catheters delivering embryos.

There is a clear clinical need for a precise catheter tracking technology for infertility treatment guidance that can deliver dense sperm count per volume to the appropriate Fallopian tube (can benefit 660,000 IUI trials/yr in the US), and deposit embryos with mm precision away from the fundus area (can benefit 165,000 IVF trials/yr in the US), leading to potential increase in success rates and reducing time/cost and hormonal intake. To gain a wide acceptance, this "smart" catheter shouldn't interrupt current clinical workflow, has to be intuitive and easy to use, works with any ultrasound vendor, and should be low-cost disposable.

Accurate tool/catheter tracking is a crucial task that directly affects the safety and effectiveness of many interventional medical procedures including infertility treatment guidance. Before exploring the proposed innovative solution of the present invention, it is important to summarize the state-of-the-art and highlight its deficiency. In recent years, several approaches have been proposed to enable tool visualization and pose recovery under US guidance including: beam steering, electromagnetic (EM) tracking, and passive markers.

The beam steering approach has been developed and validated by several research groups and currently is integrated into a commercial ultrasound scanner from SonoSite Inc. The basic principle is to steer the imaging beam directions to get the optimized reflection from the catheter/tool. It has been proven effective when the tool is rigid, in in-plane, and has acoustic impedance mismatch with surrounding tissue. For cases where catheters simply intersect the imaging plane in- and out-of-plane with a large angle, as in IUI and IVF catheters, this image enhancement method doesn't work.

An electro-magnetic (EM) tracking approach was recently introduced and integrated into several commercial ultrasound scanners (GE LOGIQ E9, Ultrasonix GPS, etc.). In this approach, an EM field is generated by an EM emitter; EM sensors are implanted in both the catheter and the imaging probe. The relative pose of the catheter is estimated and injected as a graphic overlay to the B-mode image. However, several disadvantages limit its applications to all interventions: the overall navigation accuracy can easily be worse than 3~5 mm; it requires specially designed imaging equipment to accommodate the extra H/W from the tracking system; it has an intrusive setup that interrupts the clinical workflow; it is an expensive setup that requires frequent calibration; and any ferromagnetic object in the operation region may affect the system accuracy. This technology failed to penetrate the infertility market.

Some researchers and companies focus on the visualization enhancement of the catheter in B-mode images. One approach is to improve image quality by using passive ultrasound markers. In this method, ultrasound markers, sometimes in the form of scattering coatings, are integrated into the tool to improve the echo amplitude. The major issue of this approach is that the visualization enhancement by scattering coating is limited and is affected by the insonification angle, depth and surrounding medium. These echogenic catheters exist in the infertility market (Guardia AccessET from COOK Medical). However it is impossible to identify the relative location of the tip with respect to the mid-plane of the probe. Additionally, doctors are dissatisfied from this passive technology as it only shines under specific imaging conditions.

Figure 3A:
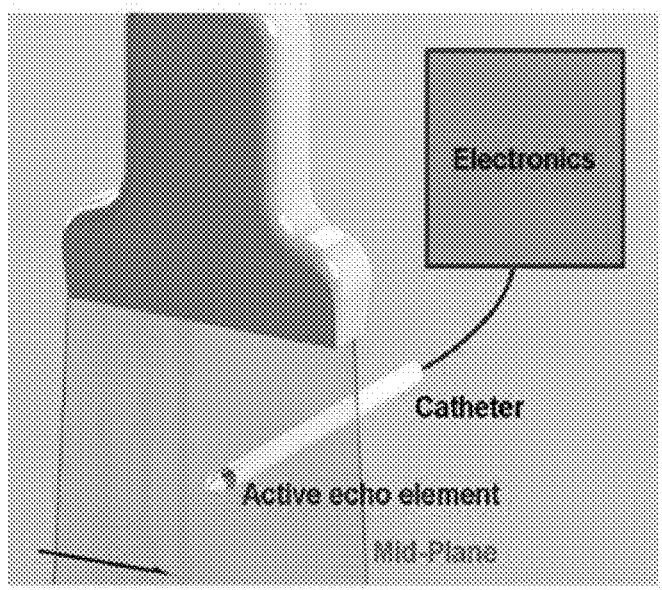
FIGS. 3A and 3B illustrate a schematic view of a configuration of the Active US Pattern Injection System (AUSPIS), according to an embodiment of the present invention.
Figure 3B:
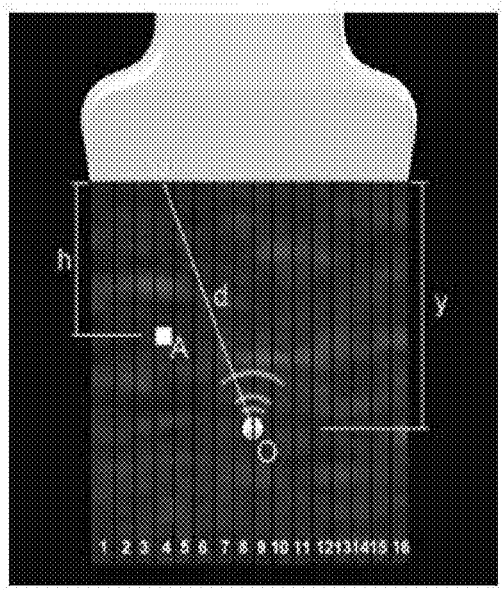

The present invention overcomes these challenges by providing a precise catheter tracking system, called Active Ultrasound Pattern Injection System (AUSPIS) (shown in FIGS. 3A and 3B and FIGS. 5A and 5B), by establishing an ultrasonic communication between any US external probe and internal catheter (CUTE catheter). The system receives the image beacon pulses, analyzes the acquired signal, and fires one or a series of active echo pulses from the same active echo element with a proper timing, frequency, duration and amplitude (FIGS. 3A and 3B). FIGS. 3A and 3B illustrate a schematic view of a configuration of the Active US Pattern Injection System (AUSPIS), according to an embodiment of the present invention. FIG. 3A illustrates that the imaging probe fires a series of ultrasound beams scanning the image region. FIG. 3B illustrates that the received pulse triggers the electronics, a driving pulse is sent to the element to fire an active echo pulse. This picture illustrates how a single virtual pixel 'A' is injected to the B-mode image from an active echo element. Thus, it enables us to inject any "virtual" pattern into the B-mode image. The pattern injected to the B mode image is from the actively encoded ultrasound field in the tissue. The encoding is based on the B-mode ultrasound image formation technique, so it doesn't require any hardware or software modification to the US machine. It continuously measures the local acoustic signal amplitude, by which sub-millimeter elevation localization accuracy can be achieved. By configuring the pattern formations, the technique can be used for tracking, tool guidance, and annotation. Additionally, the innovative 3D tracking methods are extended to be US vendor independent (Aim II), providing accurate 3D localization in- and out-of-plane. Most importantly, both H/W and S/W are designed to allow innovation in execution without interrupting the current infertility clinical protocols.

To address the clinical need described above and overcome the current technical challenges or complexities, the present invention includes a new catheter tracking platform called AUSPIS. The AUSPIS system is composed of a catheter with ultrasound tracking elements (CUTE catheter), ASUPIS control unit (ultrasound analog frontends, a signal processing system, and a pulser), and for extended range an US tracking bracket. The goal of this aim is to develop all enabling H/W components of the AUSPIS and CUTE catheters. With integration with Aim-II (Software), this novel tracking system should work with existing US systems without altering current protocols for IUI and IVF.

Figures 4A, 4B, 4C:
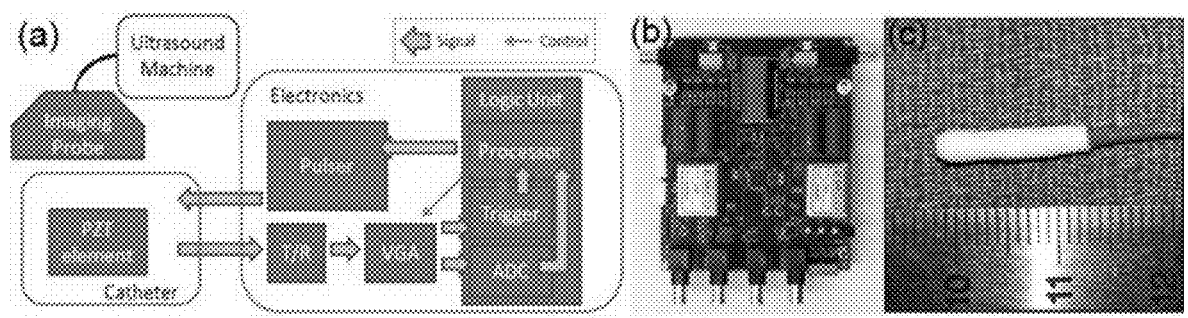
FIGS. 4A-4C illustrate schematic and image views of an AUSPIS setup, according to an embodiment of the present invention.

Active Ultrasound Pattern Injection System (AUSPIS) is shown in FIGS. 4A-4C. FIGS. 4A-4C illustrate schematic and image views of an AUSPIS setup, according to an embodiment of the present invention. FIG. 4A illustrates a schematic diagram of the AUSPIS system. FIG. 4B illustrates an image view of the pulser and logic unit board, and FIG. 4C illustrates a catheter having an active echo. A piezoelectric element for both US receiving and transmitting is integrated with a catheter. The element is connected to a customized electronic circuit, which consists of a transmit/receive (T/R) switch, a variable gain amplifier (VGA) with analog filters, triggering circuit, analog to digital converter (ADC), an embedded microprocessor, and a pulser. The T/R switch circuit is built with a TX810 8 channel integrated switch to protect the receiving circuit from the transmission driving voltage, which can go up to a hundred volts. Analog filters have a low and high cutoff frequency of 0.1 MHz and 20 MHz. The trigger circuit compares the absolute value of the signal amplitude and the threshold, and sends pulses out when it is higher than the threshold. Since the receiver and emitter are the same element, the trigger circuit has a latch and reset function to prevent oscillating triggering. The ADC converts the analog signal to digital. The control program runs on an embedded processor, which controls all the peripherals on the AUSPIS circuit. To drive the element, the pulser is able to generate pulses with a minimum duration of 12.5 ns and variable voltage from zero to ±150V.

The active echo elements developed in the previous work are based on piezoelectric effects. They are low cost, easy to fabricate and very sensitive to US signals. However, it is challenging to fabricate these elements with backing materials in a sub-millimeter catheter. In addition, these elements must be driven with electrical pulses of hundred nanoseconds duration and a voltage of 10~50 Volts. This may raise safety concerns in injecting sperms during IUI procedures or in transferring embryos in IVF procedures. To overcome these concerns, a more compact, non-electrical solution was designed and prototyped. In this prototype, all-optical design active echo elements are used, by using optical hydrophone for receiving US signals; and transmitting US waves through the photoacoustic (PA) effect.

Figure 5A:
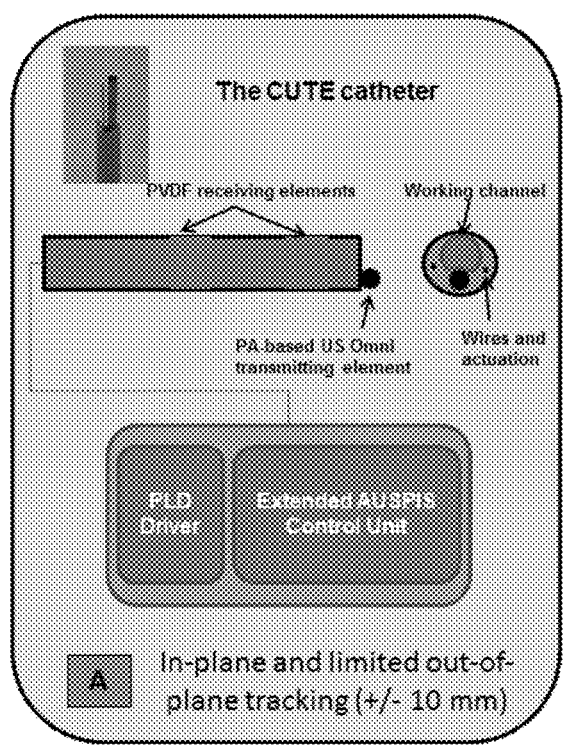
FIGS. 5A and 5B illustrate a CUTE catheter and a bracket respectively, according to an embodiment of the present invention.
Figure 5B:
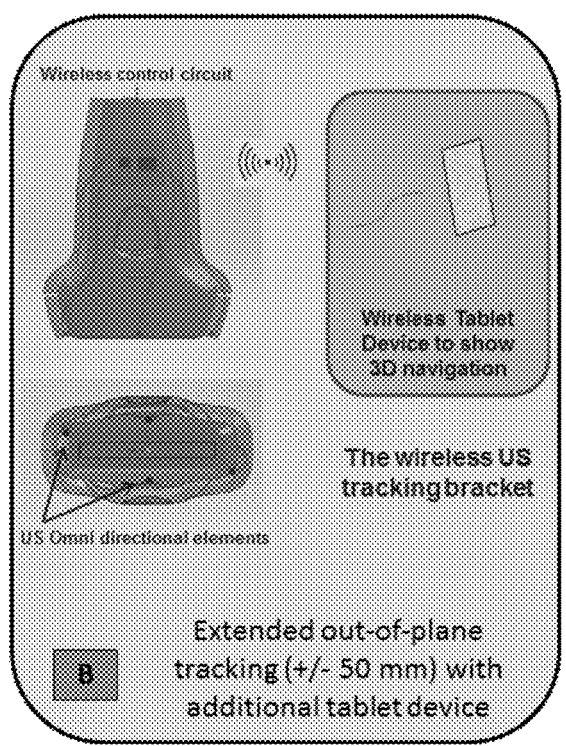

The optical hydrophone provides US sensing with limited sensitivity due to its small aperture and limited receiving angle range. Further, these optical hydrophones are expensive (~$25K-$45K). The optical hydrophone is replaced with a customized small tube made of PZTS-H or PVDF materials with an outer diameter of 1 mm and length of 2 mm. Two elements are integrated as shown on the catheter's shaft in FIG. 5A to maximize sensing sensitivity and to recover the pose of the catheter end. FIGS. 5A and 5B illustrate a CUTE catheter and a bracket respectively, according to an embodiment of the present invention. The photoacoustic element is retained as the source of transmitting Omni directional ultrasound signal, as shown in FIG. 5A. A Pulse Laser Diode (PLD) is coupled to a small optical fiber (diameter 100-200 µm), where its end is coated with a photoacoustic sensitive material as shown in FIG. 5A. Several materials can be used including India-Ink, PDMS with carbon black, or even dichroic filter that completely absorbs 532 nm wavelength and it is transparent to NIR range, allowing PA and optical biopsy usage in the future. This US transmission configuration carries several advantages. In addition to delivering an Omni directional ultrasound signal, the PLD driver can control the effective duration of the laser pulse, and therefore the effective US generated bandwidth is controllable. Most importantly, this configuration doesn't require high voltage and direct wiring to the catheter.

The AUSPIS unit is used to control a PLD driver as shown in FIG. 5A. Currently, the AUSPIS system can provide a feedback by injecting a pattern to indicate proximity to the ultrasound imaging array mid-plane, without modifying the US system or adding a new navigation screen. It is possible, however, to provide a quantitative 3D tracking if the Time-of-Flight (ToF) of the US signal between the catheter element and imaging array elements are recorded. In other words, if there is access to the channel data of the imaging array, a triangulation algorithm can be applied to track the catheter tip. Recently, this approach was implemented to test the present invention on an Ultrasonix research platform with pre-beamform data access. To overcome this limitation, and to allow this tracking algorithm to be US vendor-independent, the AUSPIS system is augmented to allow acquisition and real-time processing of received channel data from the external ultrasound imaging array. This feature eliminates the need to have a parallel beam-former on the imaging system and extend the use of this novel system to any US vendor. In summary, with the extended AUSPIS system and the CUTE catheter, the catheter tip can be tracked and the pose recovered both in-plane and out-of-plane. However, due to the elevational focusing of the imaging array and with experience in developing this novel tracking technology, the elevational capture range is limited to ~+/−10 mm.

To overcome this tracking limitation and to maintain vendor-independence requirement and low-cost execution, a tracking bracket is attached to the US imaging probe. As shown in FIG. 5B, an additional US elements is added to the commercial probe that will allow for triangulation of the position of the active echo catheter. The present invention does not to impede the normal operation of the commercial probe. Hence, the additional US elements will be developed as part of an electro-mechanical attachment to the probe. The rigidity of this attachment and its ease of fastening to the probe will allow robust registration with the image negated by the probe. FIG. 5B shows a concept of how 4 additional US elements may be positioned on the commercial probe.

The additional elements must have the following characteristics for it to work as proposed: 1) in order not to interfere with the standard imaging action of the commercial probe, the elements will operate at a different frequency and outside the sensitive range of the commercial probe. Alternatively, as described in Aim II, there is a delay between consecutive B-mode images that can be easily detected by either the bracket sensors or the CUTE catheter. This time is typically ranges from 100-500 µsec, which is sufficient for one-way US communication between the catheter and the bracket (it takes 6.5 µsec to travel 10 mm). 2) In contrast to the commercial imaging probes, the elements will have Omni-directionality for both transmission and detection. 3) The 3D position of the CUTE catheter will be computed based on the temporal and level relationships of the signal received by the 4 additional elements. 4) An additional signal detection, conditioning, digitization, and processing printed circuit board (PCB) will be used to determine the position of the catheter, and transmitted to a tablet device for visualization of navigation information.

The 4 Omni-directional elements will be composed of PZT5-H or PVDF materials. The transducers are approximately 2-3 mm in size and placed at the head of the probe so that they will be covered by the imaging gel. Four micro-wires will connect the elements to a PCB which will be positioned away from the head of the probe, and closer to the signal cable outlet. This attachment of the PCB to the commercial probe will also be designed to facilitate retrofitting to any commercial probe. The PCB will consist of custom designed circuits to a) energize the elements with a pulse frequency of 1-10 MHz and duration of hundreds of nanoseconds, b) four analog amplifiers to detect the response from the active echo catheter, c) analog to digital converters to digitize the amplified signal, d) a small Field Programmable Array (FPGA) to time stamp and process the four digitized waveforms, and e) a Wi-Fi wireless link to transmit the location of the active echo catheter to the tablet unit. The PCD will include a power source, such as a battery or a small cable connected to an AC adaptor. The circuit to detect the actively echoed signal is identical to those that are used in the active echo catheter. The main engineering effort will be directed at miniaturizing the system for easy mounting on a commercial probe, and developing the computation on the FPGA. The latter will require writing VHDL code for specific FPGA.

The rational of this algorithm is to provide real-time identification and accurate tracking of the IUI/IVF CUTE catheter with respect to the anatomy identified by the US image. It is important that the execution of these algorithms doesn't interfere with current clinical infertility treatment protocols.

Figure 6:
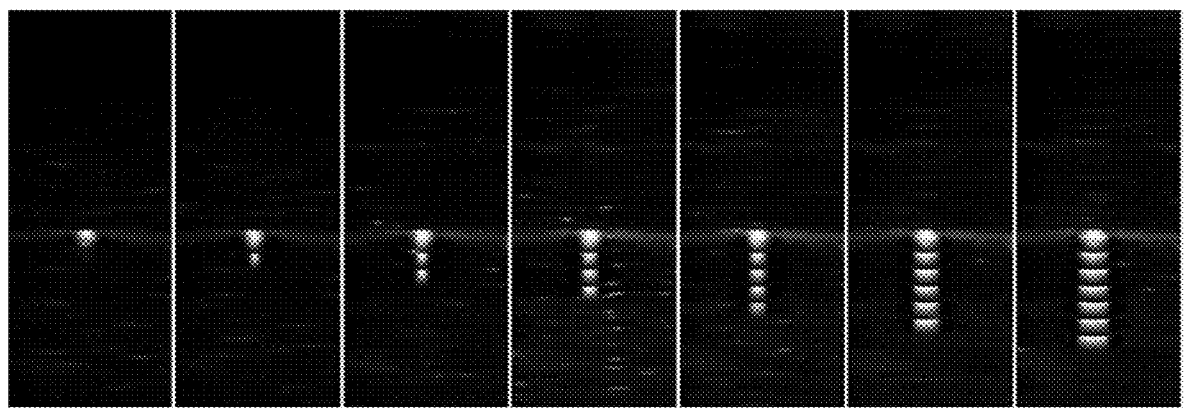
FIG. 6 illustrates an image view of a mid-plane indication using the pattern injection method, according to an embodiment of the present invention.
Figures 7A, 7B, 7C, 7D, 7E, 7F, 7G, 7H, 7I, 7J:
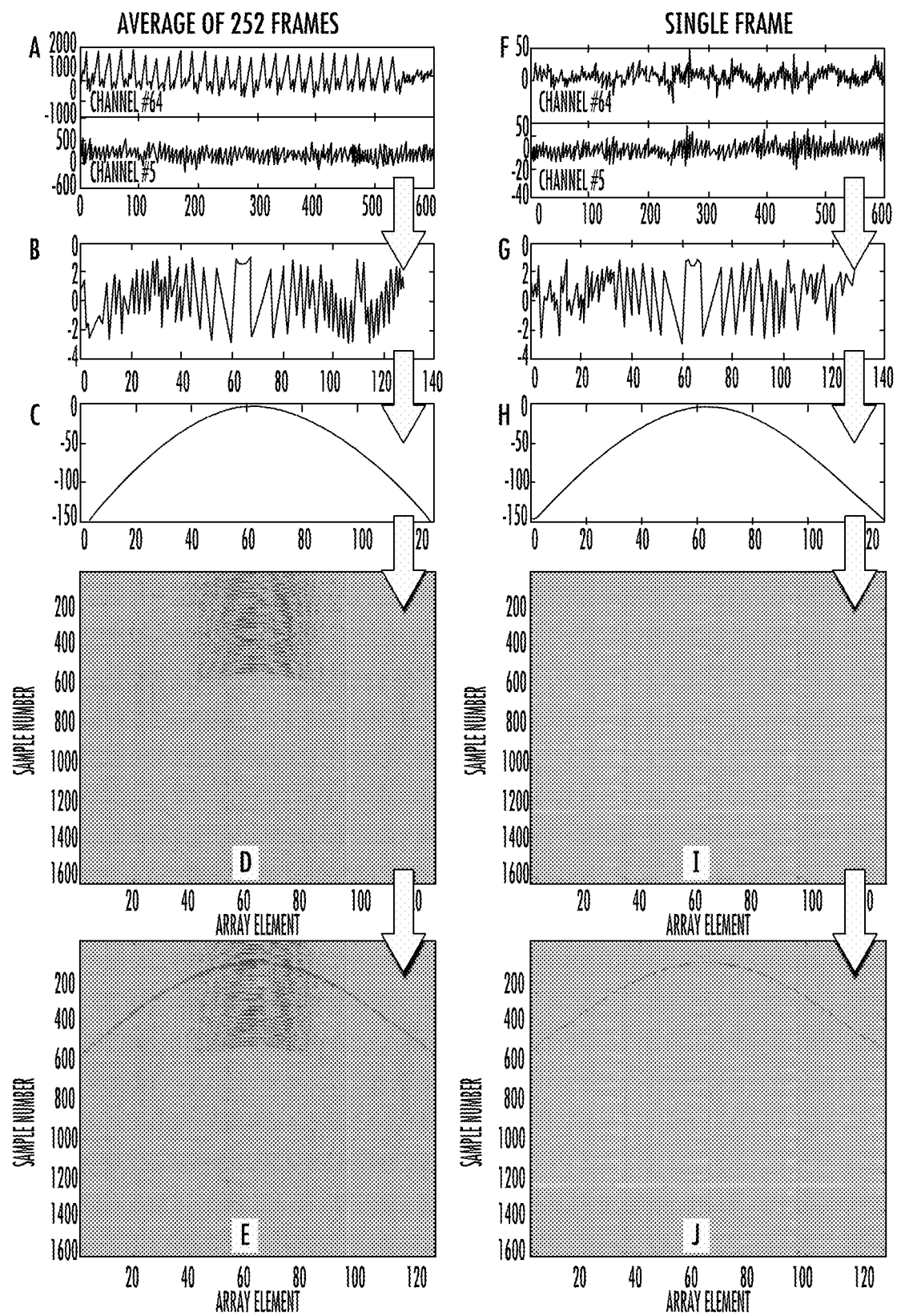
FIGS. 7A-7J illustrate graphical views of data processing procedure of the proposed unsynchronized homodyne US wavefront detection method, according to an embodiment of the present invention.

The AUSPIS system allows programmable patterns injection. The pattern injected into the image is not limited to the active-echo (AE) spot. As shown in FIG. 3B, suppose a B mode image is composed of 16 A-mode lines; the normal distance from the AE element to the probe is y. To generate a virtual spot on the point A, an ultrasound pulse should be received by the probe when the A-mode line #4 is being acquired, with a delay of: $t_{delay}=(2*h/c)$, where c is the speed of sound. The ultrasound pulse is generated from the AE element at position O, the distance between O and the center of the imaging elements R is d. The time for sound to travel from O to R is $t_{travel}=d/c$. So the timing that the element should take to send an ultrasound pulse is: $t=t_{delay}-t_{travel}=(2*h-d)/c$. In other words, if an ultrasound pulse is fired from the AE element t seconds after the probe starts acquiring the A mode line #4, it will be shown as a virtual spot at position A in the B-mode image. Having these spots as "pixels", arbitrary patterns can be formed and injected to the image. FIG. 6 shows virtual bars that are inversely proportional to the out-of-plane distance. FIG. 6 illustrates an image view of a mid-plane indication using the pattern injection method, according to an embodiment of the present invention. When the catheter moves closer to the mid-plane, the injected virtual bar increases. With this real-time feedback, the operator can easily navigate the tool tip to the ultrasound image mid-plane, which is indicated by the maximum number of bars.

The present invention also includes 3D beamforming and tracking algorithms to identify an ultrasound spot (from a catheter or PA activity) and accurately triangulate with respect to the US image frame. ToF from the available channel data was used.

Two sets of ToF data will be produced for the two elements attached on the catheter shaft, as illustrated in FIG. 5A. The calculated distance and pose will be injected on the US screen as a pattern similar to the one shown in FIG. 6, or can be easily presented on a tablet screen. Wider range of tracking requires the additional tracking bracket to be introduced, as shown in FIG. 5B.

In the extended out-of-plane tracking method, the ultrasound bracket elements receive the signal from a point ultrasound source far away from mid-plane (the Omni directional PA source on the catheter tip). The triangulation algorithm is applied to uniquely localize the catheter tip to the probe frame.

An interface to the information received by the Wi-Fi link is provided visualize the relative pose and location between the ultrasound reference to the catheter tip. Speed of sound (SoS) variation may offset the localization by 1-2% (for 10 cm depth, it can account for 1-2 mm offset). As the catheter gets closer to the main beam, SoS error will be reduced and location will be better visualized with the pattern injection system. It is also possible to correct for this error given the known rigid constraint between the PA point source and the first receiving element on the catheter shaft (very close to the PA point).

Due to distance and direction between the PA point source and bracket receiving elements, the detected signal can be very weak. To overcome this possible problem and extend the tracking range, the following signal processing approach is used: the point signal source is modulated with a predetermined frequency; the produced ultrasound wave will also be a pulse sequence with exactly the same modulation frequency. The PLD driver allows implementing such burst signal sequence. Hence, homodyne detection can be performed on the acquired signals without synchronizing T/R event. By extracting the phase and amplitude of the modulation signal from each bracket element channel, the ultrasound wavefront can be recovered. With T/R synchronization, the ToF can be measured for each receiving element, allowing triangulation as discussed before. The method is essentially a software implemented lock-in amplifier. So even in the very noisy cases, like the SNR<1, the system may still be able to extract the US wavefront.

FIGS. 7A-7J show the data processing procedures and the result comparison of the wavefront detection with different SNR. FIGS. 7A-7J illustrate graphical views of data processing procedure of the proposed unsynchronized homodyne US wavefront detection method. The right column (FIGS. 7F-7J) show the proposed data processing method with a single pre-beamforming image. The left column (FIGS. 7A-7E) shows the same method with the averaged data from 252 frames, as a comparison. Theoretically, the average will improve the data SNR by around 16 times. In the first row (FIGS. 7A and 7F), the received channel signal from element #5 and #64 are plotted. Since line #64 is closer to the photoacoustic spot, the plot shows higher signal amplitude. From FIG. 7A, channel #64 plot shows a very clear photoacoustic pulse sequence with the pre-programmed 2 MHz laser repetition frequency. On channel #5, the signal is too weak to be distinguished. In the single frame data shown in FIG. 7F, even on channel #64 the pulse sequence is not clear due to the low SNR. The second row (FIGS. 7B and 7G) shows the signal phase of the received 128 waveforms, at the frequency of 2 MHz, the laser modulation frequency. The third row (FIGS. 7C and 7H) shows the unwrapped phase. From the averaged data, the wavefront sequence can be clearly seen in the central channels that are closer to the photoacoustic signal source. From the single frame image, since the SNR is close to or lower than 1, the wavefront sequence cannot be distinguished. Conventional wavefront detection will fail with this kind of image quality. The last row plots the wavefronts detected by the proposed method on top of the pre-beamforming images. From FIG. 7E, it can be seen that the detected wavefront matches the shape of the curve on the image indicating that the wavefront is detected correctly. On the right column, although the SNR is very low, the same wavefront is also correctly detected.

For the in-plane and limited out-of-plane, 1-2 mm navigation accuracy is provided and with a frame rate higher than 10 Hz. The out-of-plane tracking range is yet to be investigated but a minimum of +/−10 mm out-of-plane is expected. For the extended tracking, 2-4 mm navigation accuracy is provided with 10 Hz update and +/−50 mm out-of-plane tracking range.

The analysis of data produced by the present invention can be carried out using a computer, non-transitory computer readable medium, or alternately a computing device or non-transitory computer readable medium incorporated into the robotic device or the imaging device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer for the ultrasound. The operating console for the ultrasound is a non-generic computer specifically designed by the manufacturer. It is not a standard business or personal computer that can be purchased at a local store. Additionally, the console computer can carry out communications with the scanner through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system, comprising:
    an external ultrasound probe;
    a catheter having an active ultrasound element for tracking the catheter,
        wherein the active ultrasound element is configured to transmit a series of pulses from the active ultrasound element to the external ultrasound probe based on detecting an ultrasound signal from the external probe,
        wherein the catheter further includes:
            a working channel for infertility treatments,
            an optical fiber, and
            at least one actuation wire, and
        wherein the optical fiber is coupled to a photoacoustic sensitive material to transmit the series of pulses omnidirectionally;
    a tracking bracket coupled to the external ultrasound probe and including a plurality of transducers configured to triangulate a position of the active ultrasound element,
        wherein the plurality of transducers are positioned adjacent to a head of the external ultrasound probe and configured to:
            transmit a signal to the active ultrasound element, and
            detect a response signal from the active ultrasound element, and
        wherein the plurality of transducers are configured to be omnidirectional;
    a printed circuit board configured to:
        energize the plurality of transducers,
        receive the response signal from the active ultrasound element,
        amplify and digitize the response signal to generate a digitized waveform,
        process the digitized waveform, and
        transmit a location of the active ultrasound element to another device; and
    one or more processors configured to:
        receive data associated with the ultrasound signal,
        receive data associated with transmission of the series of pulses, and
        analyze the data associated with the ultrasound signal and the data associated with the transmission of the series of pulses to identify an ultrasound spot corresponding to the position of the active ultrasound element within an ultrasound image frame,
            wherein a triangulation algorithm is used to identify the ultrasound spot.

2. The system of claim 1, a pulse laser diode (PLD) and a PLD driver.

3. The system of claim 2 wherein the PLD driver implements a burst signal sequence.

4. The system of claim 3, wherein the one or more processors, when analyzing the data, are further to:
    perform homodyne detection on acquired signals without synchronizing a transmit/receive (T/R) event.

5. The system of claim 1, wherein the optical fiber has a diameter of between 100-200 µm, and
    wherein the photoacoustic sensitive material comprises at least one of:
        India-ink,
        PDMS with carbon black, or
        a dichroic filter.

6. The system of claim 1, further comprising:
    one or more optical hydrophones disposed on a shaft of the catheter to maximize sensing sensitivity,
        wherein the one or more optical hydrophones are configured to receive the ultrasound signal.

* * * * *